(12) United States Patent
Choi et al.

(10) Patent No.: US 8,318,491 B2
(45) Date of Patent: Nov. 27, 2012

(54) METHOD OF DIFFERENTIATING HEMATOPOIETIC STEM CELLS INTO NATURAL KILLER CELLS USING YC-1 OR IL-21

(75) Inventors: Inpyo Choi, Taejeon-si (KR); SukRan Yoon, Taejeon-si (KR); Sohyun Yun, Taejeon-si (KR); Jin Woong Chung, Taejeon-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 321 days.

(21) Appl. No.: 12/671,814

(22) PCT Filed: Oct. 2, 2007

(86) PCT No.: PCT/KR2007/004816
§ 371 (c)(1),
(2), (4) Date: Feb. 2, 2010

(87) PCT Pub. No.: WO2009/017274
PCT Pub. Date: Feb. 5, 2009

(65) Prior Publication Data
US 2011/0033415 A1 Feb. 10, 2011

(30) Foreign Application Priority Data

Aug. 2, 2007 (KR) ........................ 10-2007-0077858

(51) Int. Cl.
*C07K 5/02* (2006.01)
*C12N 5/02* (2006.01)
*C07D 209/04* (2006.01)
(52) U.S. Cl. ........ 435/377; 435/325; 435/375; 530/351; 530/399; 548/452; 548/469
(58) Field of Classification Search ........................ None
See application file for complete search history.

(56) References Cited

U.S. PATENT DOCUMENTS

| | | | | |
|---|---|---|---|---|
| 6,929,932 B2 * | 8/2005 | Presnell et al. | | 435/69.52 |
| 8,034,326 B2 * | 10/2011 | Hjorth et al. | | 424/85.2 |
| 2004/0009150 A1 * | 1/2004 | Nelson et al. | | 424/85.2 |
| 2005/0124044 A1 * | 6/2005 | Cunningham et al. | | 435/69.5 |

OTHER PUBLICATIONS

Colucci et al. The receptor tyrosine kinase c-kit provides a critical signal for survival, expansion, and maturation of mouse natural killer cells. Blood 95(3): 984-991, 2000.*
Shibuya, A. Development and functions of natural killer cells. Int J Hematol 78: 1-6, 2003.*
Di Santo, J.P. Natural killer cell developmental pathways: a question of balance. Annu Rev Immunol 24:257-286, 2006.*
Yun et al. YC-1 enhances natural killer cell differentiation from hematopoietic stem cells. Int Immunopharmacol 10: 481-486, 2010.*
Zhang et al. Human IL-21 and IL-4 bind to partially overlapping epitopes of common gamma-chain. Biochem Biophys Res Comm 300: 291-296, 2003.*
Sivori et al. IL-21 induces both rapid maturation of human CD34+ cell precursors toward NK cells and acquisition fo surface killer Ig-like receptors. Eur J Immunol 33: 3439-3447, 2003.*
Mrozek et al. Role of interleukin-15 in the development of human CD56+ natural killer cells from CD34+ hematopoietic progenitor cells. Blood 87: 2632-2640, 1996.*
Bordignon et al., "Cell therapy: achievements and perspectives," *Haematologica*, vol. 84, pp. 1110-1149, 1999.
Brady et al., "IL-21 Induces the Functional Maturation of Murine NK Cells," *Journal of Immunology*, vol. 172, pp. 2048-2058, 2004.
Chun et al., "Inhibitory effect of YC-1 on the hypoxic induction of erythropoietin and vascular endothelial growth factor in Hep3B cells," *Biochemical Pharmacology*, vol. 61, pp. 947-954, 2001.
Ensminger et al., "Critical Role for IL-4 in the Development of Transplant Arteriosclerosis in the Absence of CD40-CD154 Costimulation," *Journal of Immunology*, vol. 167, pp. 532-541, 2001.
Funasaka et al., "Regulation of phosphoglucose isomerase/autocrine motility factor expression by hypoxia," *FASEB Journal*, vol. 19, pp. 1422-1430, 2005.
Galle et al., "Effects of the soluble guanylyl cyclase activator, YC-1, on vascular tone, cyclic GMP levels and phosphodiesterase activity," *British Journal of Pharmacology*, vol. 127, pp. 195-203, 1999.
Itoh et al., "Lysis of human solid tumor cells by lymphokine-activated natural killer cells," *Journal of Immunology*, vol. 136, pp. 3910-3915, 1986.
Ko et al., "YC-1, a Novel Activator of Platelet Guanylate Cyclase," *Blood*, vol. 84, No. 12, pp. 4226-4233, 1994.
Konjević et al., "Association of NK cell dysfunction with changes in LDH characteristics of peripheral blood lymphocytes (PBL) in breast cancer patients," *Breast Cancer Research and Treatment*, vol. 66, pp. 255-263, 2001.
Leonard and Spolski, "Interleukin-21: A Modulator of Lymphoid Proliferation, Apoptosis and Differentiation," *Nature*, vol. 5, pp. 688-698, 2005.
Moeller et al., "Radiation activates HIF-1 to regulate vascular radiosensitivity in tumors: Role of reoxygenation, free radicals, and stress granules," *Cancer Cell*, vol. 5, pp. 429-441, 2004.
Moroz et al., "IL-21 Enhances and Sustains CD8+ T Cell Responses to Achieve Durable Tumor Immunity: Comparative Evaluation of IL-2, IL-15, and IL-21," *Journal of Immunology*, vol. 173, pp. 900-909, 2004.
Pan et al., "YC-1 [3-(5'-Hydroxymethyl-2'-furyl)-1-benzyl Indazole] Inhibits Endothelial Cell Functions Induced by Angiogenic Factors in Vitro and Angiogenesis in Vivo Models," *Journal of Pharmacology and Experimental Therapeutics*, vol. 314, No. 1, pp. 35-42, 2005.

(Continued)

Primary Examiner — Bridget E Bunner
(74) Attorney, Agent, or Firm — Klarquist Sparkman, LLP.

(57) ABSTRACT

The present invention relates to an agent for differentiating hematopoietic stem cells into natural killer cells and a method for the differentiation, more precisely an agent for differentiating hematopoietic stem cells into natural killer cells comprising YC-I [3-(5'-hydroxymethyl-2'-furyl)-1-benzylindazole] or IL-21 (Interleukin-21) as an active ingredient and a method for differentiating hematopoietic stem cells into natural killer cells using the same. The YC-I and IL-21 regulate the differentiation of hematopoietic stem cells into natural killer cells and increase the killing activity of NK cells. Therefore, the agent for NK cell differentiation of the present invention can be effectively used for cell therapy for the treatment of cancer by regulating the differentiation of hematopoietic stem cells into natural killer cells having tumor cell killing activity.

5 Claims, 11 Drawing Sheets

OTHER PUBLICATIONS

Parrish-Novak et al., "Interleukin 21 and its receptor are involved in NK cell expansion and regulation of lymphocyte function," *Nature*, vol. 408, pp. 57-63, 2000.

Perez et al., "Effect of IL-21 on NK cells derived from different umbilical cord blood populations," *International Immunology*, vol. 18, No. 1, pp. 49-58, 2005.

Strengell et al., "IL-21 in Synergy with IL-15 or IL-18 Enhances IFN-{gamma} Production in Human NK and T Cells," *Journal of Immunology*, vol. 170, pp. 5464-5469, 2003.

Sun et al., "YC-1 inhibits HIF-1 expression in prostate cancer cells: contribution of Akt/NF-κB signaling to HIF-1α accumulation during hypoxia," *Oncogene*, vol. 26, pp. 3941-3951, 2007.

Takaki et al., "IL-21 Enhances Tumor Rejection through a NKG2D-Dependent Mechanism," *Journal of Immunology*, vol. 175, pp. 2167-2173, 2005.

Teng et al., "YC-1, a nitric oxide-independent activator of soluble guanylate cyclase, inhibits platelet-rich thrombosis in mice," *European Journal of Pharmacology*, vol. 320, pp. 161-166, 1997.

Villegas et al., "Prognostic significance of tumor infiltrating natural killer cells subset CD57 in patients with squamous cell lung cancer," *Lung Cancer*, vol. 35, pp. 23-28, 2002.

Yeo et al., "YC-1: A Potential Anticancer Drug Targeting Hypoxia-Inducible Factor 1," *Journal of the National Cancer Institute*, vol. 95, No. 7, pp. 516-525, 2003.

Yeo et al., "YC-1 Induces S Cell Cycle Arrest and Apoptosis by Activating Checkpoint Kinases," *Cancer Research*, vol. 66, No. 12, pp. 6345-6352, 2006.

\* cited by examiner

METHOD OF DIFFERENTIATING HEMATOPOIETIC STEM CELLS INTO NATURAL KILLER CELLS USING YC-1 OR IL-21

CROSS REFERENCE TO RELATED APPLICATIONS

This is the §371 U.S. National Stage of International Application No. PCT/KR2007/004816, filed Oct. 2, 2007, which was published in English under PCT Article 21(2), which in turn claims the benefit of Korean Patent Application No. 10-2007-0077858, filed Aug. 2, 2007.

TECHNICAL FIELD

The present invention relates to an agent for differentiating hematopoietic stem cells into natural killer cells and a method thereof, more precisely an agent for differentiating hematopoietic stem cells into natural killer cells comprising YC-1 [3-(5'-hydroxymethyl-2'-furyl)-1-benzylindazole] or IL-21 (Interleukin-21) as an active ingredient and a method for differentiating hematopoietic stem cells into natural killer cells using the same.

BACKGROUND ART

Hematopoietic stem cells, kind of adult stem cells, have a potential for differentiating into almost every blood forming cells (including erythrocytes, leucocytes, platelets and lymphocytes) and are constantly auto-regenerated as immune cells from the hematopoietic stem cell in bone marrow. The cells forming immune system, in particular natural killer cells (referred as "NK cells" hereinafter), have an ability to kill tumor cells non-specifically.

This tumor cell killing activity of NK cells has been used for the treatment of a solid tumor using lymphokine activated killer cells (LAK) and tumor infiltration lymphocytes (TIL) or for the immune therapy via donor lymphocyte infusion (Itoh K, et al., *J. Immunol.*, 136: 3910-3915, 1986; Bordignon C, et al., *Hematologia*, 84: 1110-1149, 1999), which has drawn our attention as an advanced cell therapy for preventing rejection from bone marrow transplantation or organ transplantation. It was also reported that the defect in NK cell differentiation or activity is related to various diseases including breast cancer (Konjevic G, et al., Breast Cancer Res. Treat., 66: 255-263, 2001), melanoma (Ryuke Y, et al., *Melanoma Res.*, 13: 349-356, 2003) and lung cancer (Villegas F R, et al., Lung Cancer, 35: 23-28, 2002). So, correction of NK cell functions seems to lead the way to treat these diseases.

NK cells are derived from hematopoietic stem cells in bone marrow. The differentiation from hematopoietic stem cells into NK cells is composed of many steps, which have not been completely explained, yet.

IL-21 (Interleukin-21) is a cytokine secreted by activated CD4+ T cells (Warren J., et al., *Nature*, 5: 688-697, 2005). IL-21 receptor (IL-21R) is expressed in lymphocytes such as dendrite cells, NK, T, and B cells (Takaki R., et al., *J. Immunol.*, 175: 2167-2173, 2005). The structure of IL-21 is very similar to those of IL-2 and IL-15, and IL-21R shares γ-chain with IL-2R, IL-15, IL-7R or IL-4R (Ensminger S M, et al., *J. Immunol.* 167 (1):532-541, 2001).

According to the previous reports, IL-21 induces maturation of NK cell precursor in bone marrow (Parrish-Novak J., et al., *Nature*, 408: 57-63, 2000) and characteristically increases effector functions of NK such as cytokine generation ability and killing activity (Strengell M, et al., *J. Immunol.*, 170: 5464-5469, 2003; Brady J, et al., *J. Immunol.*, 172: 2048-2058, 2004). IL-21 also increases effector functions of CD8+ T cells, leading to the promotion of anticancer response of innate or adaptive immune system (Takaki R., et al., *J. Immunol.*, 175: 2167-2173, 2005; Moroz A., et al., *J Immunol*, 173: 900-909, 2004). In addition, IL-21 activates NK cells separated from human peripheral blood (Parrish-Novak J., et al., Nature, 408: 57-63, 2000) and plays an important role in differentiation of NK cells from hematopoietic stem cells separated from umbilical cord blood (Sonia A. P, et al., *Int. immunol.*, 18: 49-58, 2006).

YC-1 [3-(5'-hydroxymethyl-2'-furyl)-1-benzylindazole] was first developed as an agent for treating circulatory diseases after it was proved to inhibit coagulation of platelets and activate soluble GC (guanylyl cyclase) to inhibit contraction of blood vessel (Ko F N, et al., *Blood* 84. No. 12:4226-4233 1994; Teng C M, et al., *Eur J Pharmacol*, 320:161-6, 1997; Galle J., et al., *Br J Pharmacol*, 127: 195-203, 1999). It was additionally found in recent studies that it inhibits HIF-1α accumulation induced in hypoxia, reduces expressions of HIF-1 target genes (VEGF, erythropoietin, etc.) (Chun Y S, et al., *Biochem Pharmacol*, 61:947-954, 2001), and inhibits tumor growth and angiogenesis in animals (Yeo E J, et al., *J Natl Cancer Inst*, 95: 516-525, 2003; Pan S L, et al., *J pharmacol Exp Ther*, 314:35-42, 2005). So, YC-1 becomes a leading compound for the development of an anticancer agent targeting HIF-1α (Yeo E J, et al., *Cancer Res*, 66: 6345-6352, 2006). Even though YC-1 is very useful for the study of HIF-1α (Moeller B J, et al., *Cancer cell* 5: 429-441, 2004; Funasaka T, et al., FASEB J, 19:1422-1430, 2005), the mechanism of anticancer activity of YC-1 has not been disclosed, yet (Sun. H. L., et. al. *Oncogene* 1-11, 2006).

The present inventors completed this invention by confirming that IL-21 (Interleukin-21) and YC-1 [3-(5'-hydroxymethyl-2'-furyl)-1-benzylindazole] promote the differentiation of hematopoietic stem cells into natural killer cells and increase the killing activity of natural killer cells.

DISCLOSURE

Technical Problem

It is an object of the present invention to provide an agent for differentiating hematopoietic stem cells into natural killer cells and a method for the differentiation.

Technical Solution

To achieve the above object, the present invention provides an agent for differentiating hematopoietic stem cells into natural killer cells comprising YC-1 [3-(5'-hydroxymethyl-2'-furyl)-1-benzylindazole] as an active ingredient.

The present invention also provides an anticancer agent comprising IL-21 (Interleukin-21) as an active ingredient.

The present invention further provides an agent for differentiating hematopoietic stem cells into natural killer cells comprising YC-1 [3-(5'-hydroxymethyl-2'-furyl)-1-benzylindazole] and IL-21 (Interleukin-21) as active ingredients.

The present invention also provides an anticancer agent comprising YC-1 [3-(5'-hydroxymethyl-2'-furyl)-1-benzylindazole] and IL-21 (Interleukin-21) as active ingredients.

The present invention also provides a method for differentiating hematopoietic stem cells into natural killer cells using IL-21 and/or YC-1.

The present invention also provides a cell therapy method for the treatment of cancer, containing the step of administering natural killer cells differentiated by the above method to tumor cells.

The present invention also provides a method for increasing the killing activity of NK cells, containing the step of administering IL-21 (Interleukin-21) to hematopoietic stem cells.

The present invention also provides a method for increasing the killing activity of NK cells, containing the step of administering YC-1 [3-(5'-hydroxymethyl-2'-furyl)-1-benzylindazole] to hematopoietic stem cells.

The present invention also provides a method for increasing the killing activity of NK cells, containing the step of administering YC-1 [3-(5'-hydroxymethyl-2'-furyl)-1-benzylindazole] and IL-21 (Interleukin-21) to hematopoietic stem cells.

The present invention also provides a cell therapy method for the treatment of cancer, containing the step of administering natural killer cells with the improved tumor cell killing activity to tumor cells.

The present invention also provides a use of YC-1 for the preparation of an agent for differentiating hematopoietic stem cells into natural killer cells or an anticancer agent.

The present invention also provides a use of IL-21 for the preparation of an anticancer agent.

In addition, the present invention provides a use of YC-1 and IL-21 for the preparation of an agent for differentiating hematopoietic stem cells into natural killer cells or an anticancer agent.

Advantageous Effect

YC-1 and IL-21 are involved in NK cell differentiation and increase the killing activity of NK cells. So, an agent for differentiating hematopoietic stem cells into natural killer cells comprising YC-1 or IL-21 as an active ingredient and an anticancer agent comprising IL-21 as an active ingredient can be effectively used for the development of a novel method for cell therapy for cancer and for the regulation of NK cell differentiation.

DESCRIPTION OF DRAWINGS

The application of the preferred embodiments of the present invention is best understood with reference to the accompanying drawings, wherein.

Precisely, in NK differentiation, IL-21 was treated to pNKs, which were cultured in the presence of IL-15 and CD56+ NK cells were counted over cultivation time.

Figure 6:
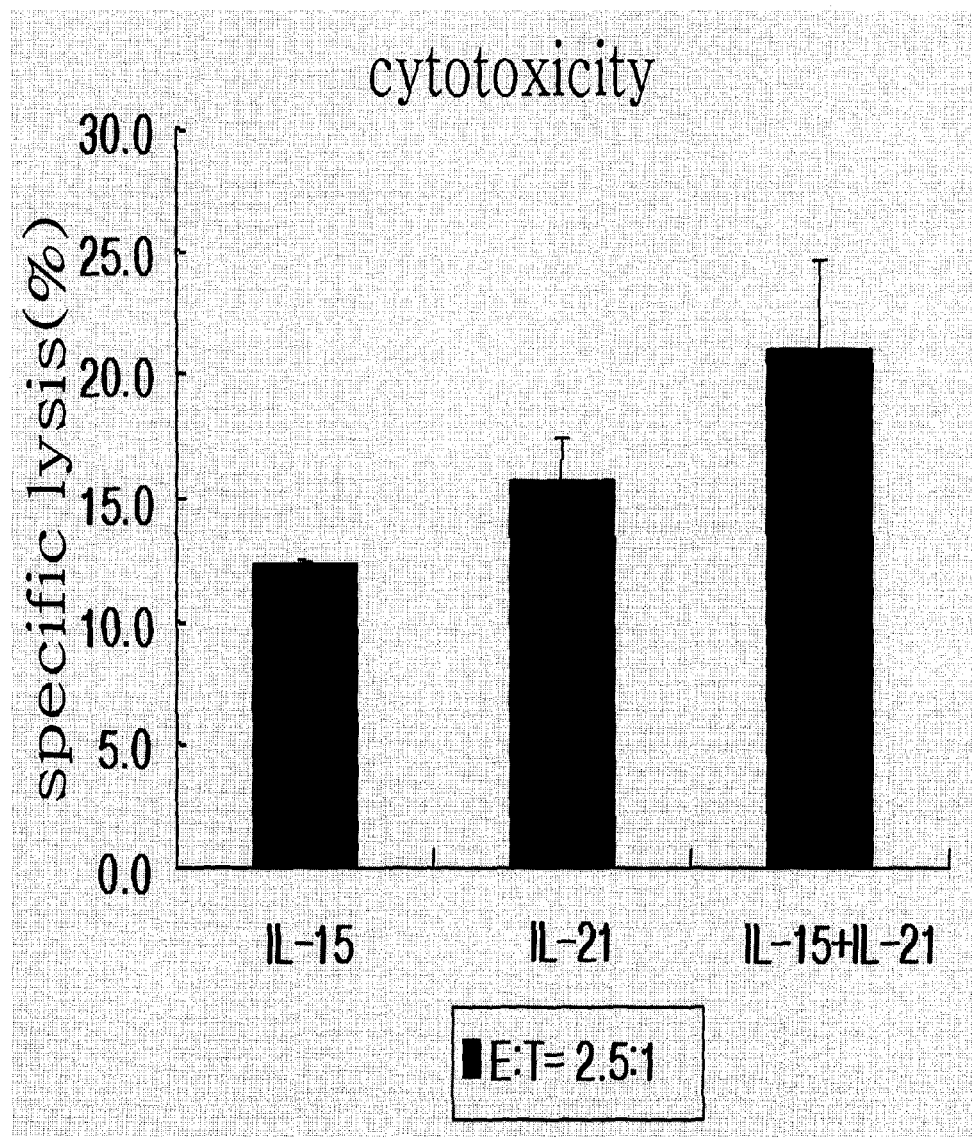

FIG. 6 is a graph illustrating the result of $^{51}$Cr release assay. In NK differentiation, IL-21 was treated to pNKs, which were cultured in the presence of IL-15 until they became differentiated into mature NK (mNK) cells, followed by $^{51}$Cr release assay:
E:T: effector cell:target cell.

Figure 7:
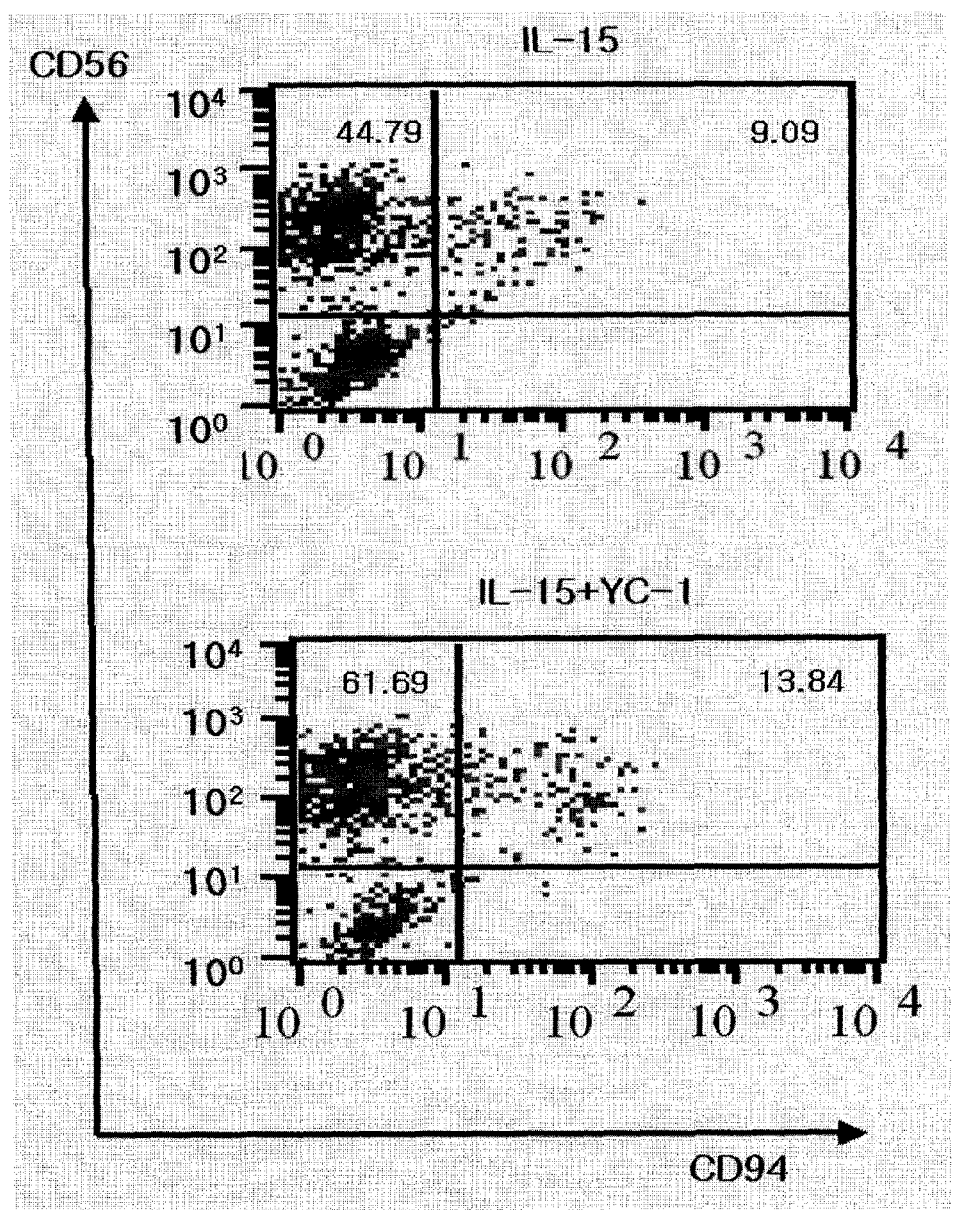

FIG. 7 is a graph illustrating the result of FACS analysis. In NK differentiation, YC-1 was treated to pNKs, which were cultured in the presence of IL-15 until they became differentiated into mature NK (mNK) cells, followed by FACS.

Figure 8:
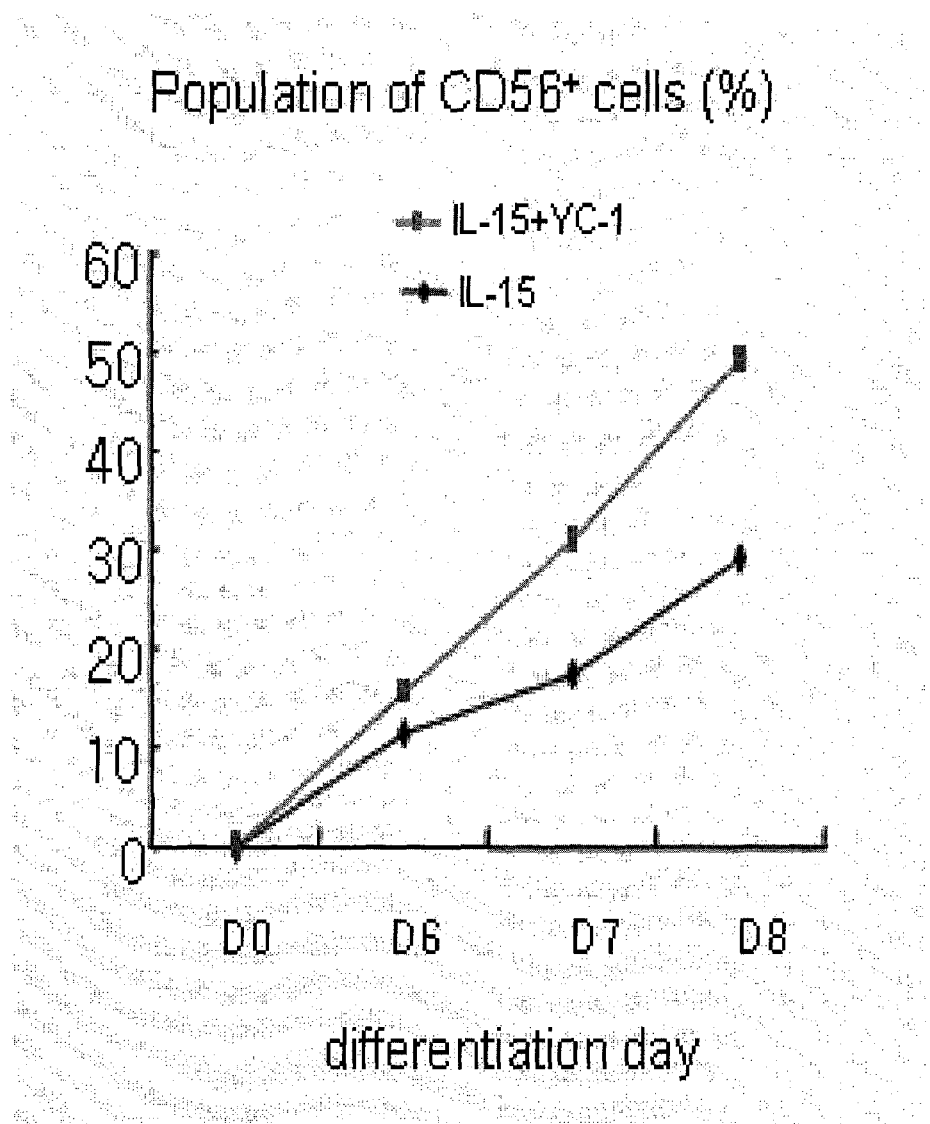

FIG. 8 is a graph illustrating the population of CD56+ NK cells. Precisely, in NK differentiation, YC-1 was treated to pNKs, which were cultured in the presence of IL-15. CD56+ NK cells were counted over the cultivation time and represented by %.

Figure 9:
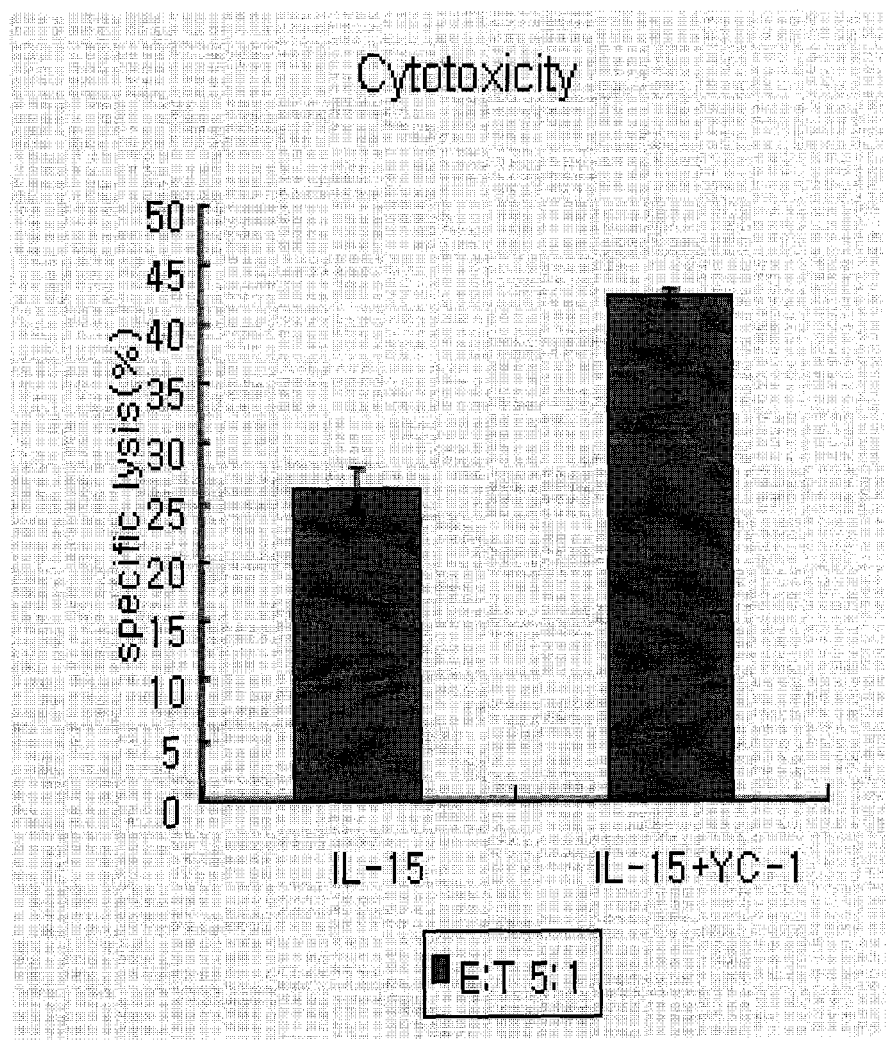

FIG. 9 is a graph illustrating the result of $^{51}$Cr release assay. In NK differentiation, YC-1 was treated to pNKs, which were cultured in the presence of IL-15 until they became differentiated into mature NK (mNK) cells, followed by $^{51}$Cr release assay:
E:T: effector cell:target cell.

Figure 10:
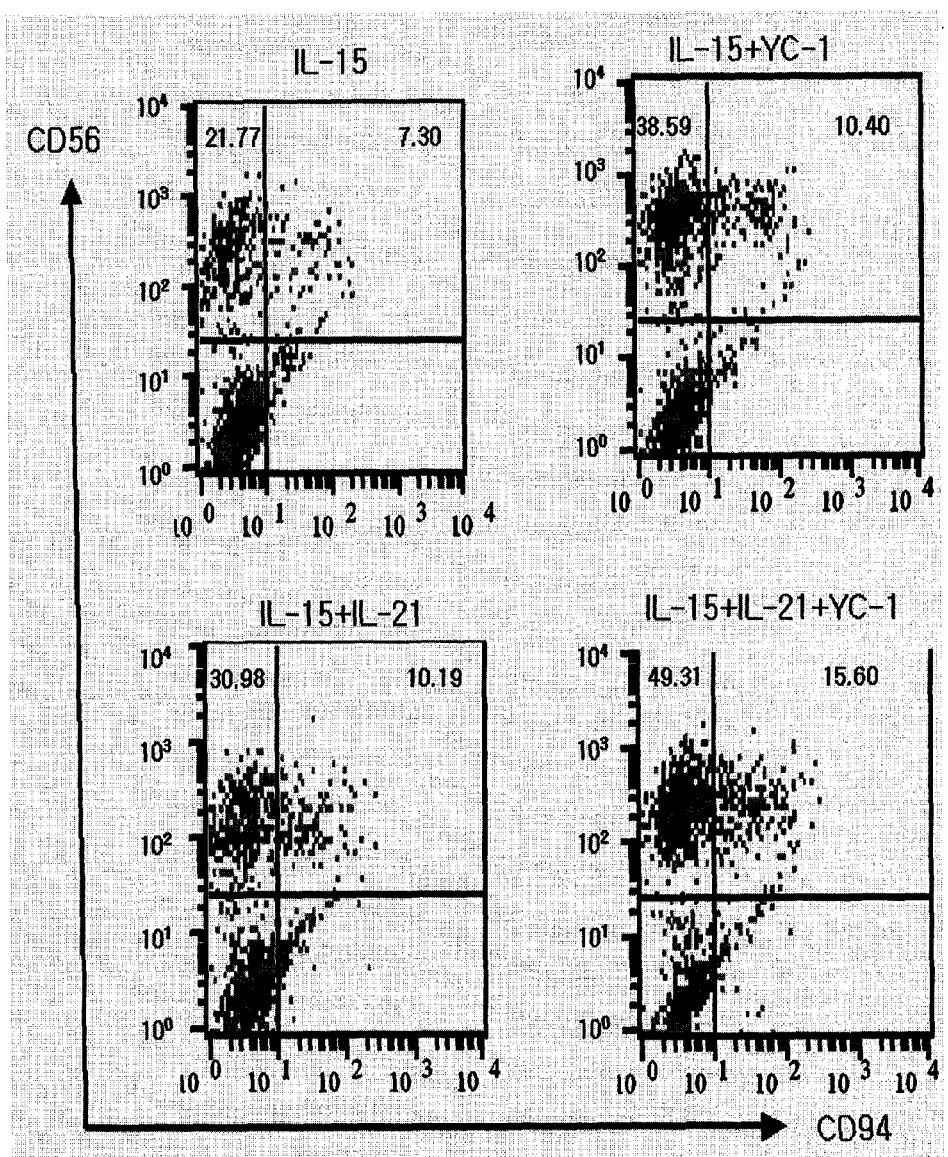

FIG. 10 is a graph illustrating the result of FACS analysis. In NK differentiation, both IL-21 and YC-1 were treated to pNKs, which were cultured in the presence of IL-15 until they became differentiated into mature NK (mNK) cells, followed by FACS.

Figure 11:
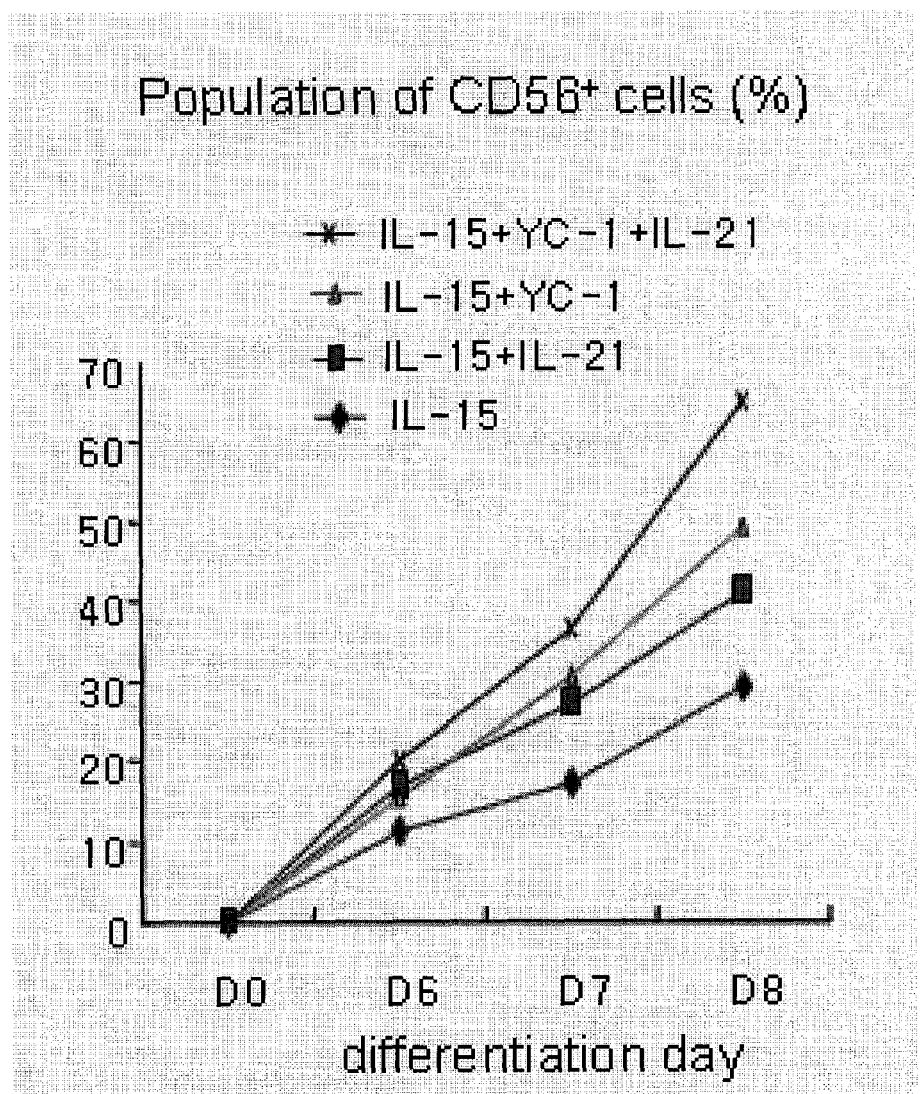

FIG. 11 is a graph illustrating the population of CD56+ NK cells over cultivation time. In NK differentiation, both IL-21 and YC-1 were treated to pNKs, which were cultured in the presence of IL-15, followed by measuring the population of CD56+ NK cells over cultivation time.

MODE FOR INVENTION

Hereinafter, the present invention is described in detail.

The present invention provides an agent for differentiating hematopoietic stem cells into natural killer cells comprising YC-1 [3-(5'-hydroxymethyl-2'-furyl)-1-benzylindazole] as an active ingredient.

The YC-1 ($C_{19}H_{16}N_2O_2$) is represented by formula 1.

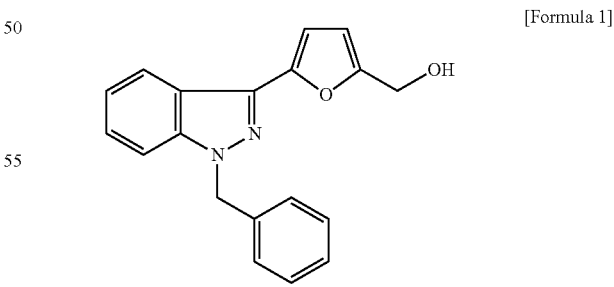

[Formula 1]

The present invention also provides an anticancer agent comprising IL-21 (Interleukin-21) as an active ingredient.

The IL-21 (Interleukin-21) is preferably selected from the group consisting of (a) the protein comprising the amino acid sequence represented by SEQ. ID. NO: 1; (b) the protein encoded by the DNA containing the coding region of the nucleotide sequence represented by SEQ. ID. NO: 2; (c) the protein comprising the amino acid sequence with substitution, deletion, insertion and/or addition of one or more amino acids in the amino acid sequence represented by SEQ. ID. NO: 1 and is functionally equal to the protein comprising the amino acid sequence represented by SEQ. ID. NO: 1; and (d) the protein encoded by the DNA hybridized with the DNA comprising the nucleotide sequence represented by SEQ. ID. NO: 2 under the strict condition and is functionally equal to the protein comprising the amino acid sequence represented by SEQ. ID. NO: 1.

Hybridization under the strict condition enables the selection of DNA having the nucleotide sequence with high homology. Thus, the chances are high for the separated protein therefrom to be a protein that is functionally equal to IL-21. The nucleotide sequence with high homology means, for example, the nucleotide sequence having at least 70% homology with the nucleotide sequence represented by SEQ. ID. NO: 2, preferably having at least 80% homology and more preferably at least 90% and most preferably at least 95% homology with the nucleotide sequence represented by SEQ. ID. NO: 2. In the case of amino acid sequence, the amino acid sequence having at least 70% homology, preferably at least 80% homology, more preferably at least 90% and most preferably at least 95% homology with the amino acid sequence represented by SEQ. ID. NO: 1 can be selected. The percent of homology can be determined by the conventional algorithm selected by those in the art.

The hybridization can be performed by DNA-DNA hybridization under the strict condition (Hames and Higgins, Eds. (1985) Nucleic Acid Hybridization, IRL Press, U.K.) known to those in the art and the condition can be determined in the washing process after hybridization.

The present invention further provides an agent for differentiating hematopoietic stem cells into natural killer cells comprising YC-1 [3-(5'-hydroxymethyl-2'-furyl)-1-benzylindazole] and IL-21 (Interleukin-21) as active ingredients.

Figure 1:
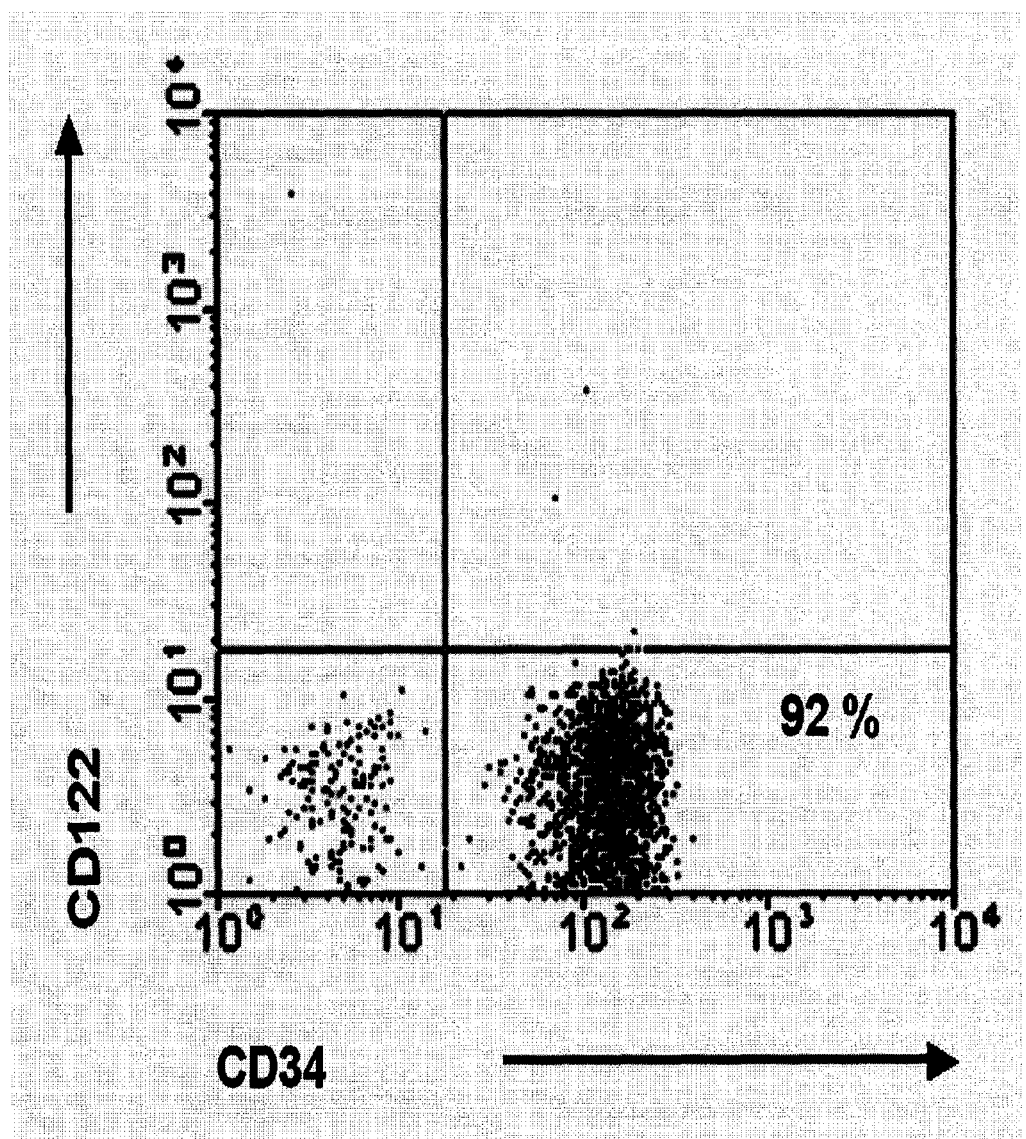
FIG. 1 is a graph illustrating the purity of CD34+ hematopoietic stem cells measured by flow cytometry (the number written in quadrant indicates the purity).

The present inventors separated CD34+ hematopoietic stem cells (referred as "HSC cells" hereinafter) with 92% purity from cord blood (see FIG. 1). The HSC cells were differentiated into mature NK cells through pNKs (see FIG. 2) and the expression of the surface molecule was examined for each NK cell differentiation stage (see FIG. 3). As a result, CD56 cells were increased.

In NK cell differentiation, IL-21 was treated to pNKs, which were cultured in the presence of IL-15 to differentiate pNKs into mNK cells. FACS analysis was performed. As a result, CD56+ NK cell population was increased in IL-21 treated group, compared with the IL-21 non-treated control (treated with IL-15 alone) (see FIGS. 4 and 5), suggesting that IL-21 was involved in NK differentiation. From the result of $^{51}$Cr release assay, it was confirmed that IL-21 treated group exhibited increased killing activity, compared with IL-21 non-treated group (treated with IL-15 alone) (see FIG. 6), suggesting that IL-21 was involved in the activation of the killing activity of NK cells.

NK precursor cells (pNK) were treated with YC-1 and cultured in the presence of IL-15 to differentiate into matured NK (mNK) cells, followed by FACS analysis. As a result, CD56+ NK cells were increased in YC-1 treated group, compared with YC-1 non-treated group (treated with IL-15 alone) (see FIGS. 7 and 8), suggesting that YC-1 was involved in NK cell differentiation. From the result of $^{51}$Cr release assay, it was confirmed that YC-1 treated group exhibited increased killing activity, compared with IL-21 non-treated group (treated with IL-15 alone) (see FIG. 9), suggesting that YC-1 was involved in the activation of the killing activity of NK cells.

NK precursor cells (pNK) were treated with both IL-21 and YC-1 at the same time and NK cell differentiation was investigated. As a result, NK cell differentiation was significantly increased (see FIGS. 10 and 11).

As explained hereinbefore, IL-21 and YC-1 promote differentiation from hematopoietic stem cells into natural killer cells and increase the killing activity of NK cells, so that they can be effectively used as agents for differentiating hematopoietic stem cells into NK cells.

The present invention also provides an anticancer agent comprising YC-1 [3-(5'-hydroxymethyl-2'-furyl)-1-benzylindazole] and IL-21 (Interleukin-21) as active ingredients.

The agent for differentiating into NK cells and the anticancer agent of the invention can be used for cell therapy for the treatment of cancer.

The cancer herein is preferably selected from the group consisting of breast cancer, melanoma, stomach cancer, liver cancer, blood cancer, colon cancer, and lung cancer, but not always limited thereto.

If there is a defect in the differentiation and activity of NK cells, various cancers might be developed, for example, breast cancer (Konjevic G, et al., *Breast Cancer Res. Treat.*, 66: 255-263, 2001), melanoma (Ryuke Y, et al., *Melanoma Res.*, 2003, 13: 349-356) and lung cancer (Villegas F R, et al., *Lung Cancer*, 35: 23-28, 2002), etc, according to the previous reports. Therefore, it is expected to treat such cancers as the above by regulating NK cell differentiation using the agent for NK cell differentiation and the anticancer agent of the invention.

The agent for NK cell differentiation and the anticancer agent of the present invention can be administered orally or parenterally and be used in general forms of pharmaceutical formulation. The agent for NK cell differentiation and the anticancer agent of the present invention can be prepared for oral or parenteral administration by mixing with generally used fillers, extenders, binders, wetting agents, disintegrating agents, diluents such as surfactant, or excipients. Solid formulations for oral administration are tablets, pills, dusting powders, granules and capsules. These solid formulations are prepared by mixing one or more suitable excipients such as starch, calcium carbonate, sucrose, lactose, gelatin, etc. Except for the simple excipients, lubricants, for example magnesium stearate, talc, etc, can be used. Liquid formulations for oral administrations are suspensions, solutions, emulsions and syrups, and the above mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the agent for NK cell differentiation or the anticancer agent of the present invention is 0.1~0.2 mg/kg, and more preferably 0.15 mg/kg, and the administration times are preferably 1~3 times a day.

The present invention also provides a method for differentiating hematopoietic stem cells into natural killer cells using IL-21 and/or YC-1.

Particularly, the method for differentiating hematopoietic stem cells into NK cells comprises the following steps:

1) inducing proliferation of NK precursor cells by adding a NK precursor inducer to hematopoietic stem cells; and
2) differentiating the NK precursor cells into mature NK cells by adding IL-21 and/or YC-1 to the NK precursor cells of step 1).

In step 1), the "NK precursor inducer" means any substance that is able to induce differentiation from hematopoietic stem cells into NK precursor cells, which is preferably SCF or Flt3L, but not always limited thereto.

In step 2), the preferable treatment amount of IL-21 is 10 ng/ml~50 ng/ml, and the treatment amount of YC-1 is 0.5 uM~5 uM. In the case of co-treatment of YC-1 and IL-21, preferable contents of YC-1 and IL-21 are respectively 0.5 uM and 10 ng/ml, but not always limited thereto.

In step 2), the NK precursor cells are preferably cultured with IL-15 (Interleukin-15), but not always limited thereto.

According to the conventional method, hematopoietic stem cells separated from cord blood are treated with IL-15 and IL-21 simultaneously to induce proliferation and differentiation at the same time. So, differentiation speed is very slow and thus takes long time (30 days). However, in the method of the present invention, differentiation from hematopoietic stem cells into NK precursor cells is first induced by adding SCF and Flt3L and then differentiation into mature NK cells is induced by adding IL-15 and IL-21 and/or YC-1, which makes the method efficient and reduces differentiation time (14 days).

The present invention also provides a cell therapy method for the treatment of cancer, containing the step of administering natural killer cells differentiated by the above method to tumor cells.

The differentiation from hematopoietic stem cells into NK cells above is induced in vitro.

The cancer herein is preferably selected from the group consisting of breast cancer, melanoma, stomach cancer, liver cancer, blood cancer, colon cancer, and lung cancer, but not always limited thereto.

To induce differentiation from hematopoietic stem cells into NK cells, YC-1 or IL-21 can be administered but co-administration of YC-1 and IL-21 is preferred.

The present invention also provides a method for increasing the killing activity of NK cells, containing the step of administering IL-21 (Interleukin-21) to hematopoietic stem cells.

The effective dosage of IL-21 is 10 ng/ml~50 ng/ml, and is preferably administered together with IL-15 (Interleukin-15) for the culture, but not always limited thereto.

The present invention also provides a method for increasing the killing activity of NK cells, containing the step of administering YC-1 [3-(5'-hydroxymethyl-2'-furyl)-1-benzylindazole] to hematopoietic stem cells.

The preferable dosage of YC-1 is 0.5 uM~5 uM, and is preferably administered together with IL-15 (Interleukin-15) for the culture, but not always limited thereto.

The present invention also provides a method for increasing the killing activity of NK cells, containing the step of administering YC-1 [3-(5'-hydroxymethyl-2'-furyl)-1-benzylindazole] and IL-21 (Interleukin-21) to hematopoietic stem cells.

The preferable hematopoietic stem cells for the invention are those who are under-going differentiation into NK cells.

The preferable doses of YC-1 and IL-21 are respectively 0.5 uM and 10 ng/ml, which are preferably co-treated with IL-15 (Interleukin-15) for the culture of hematopoietic stem cells, but not always limited thereto.

The present invention also provides a cell therapy method for the treatment of cancer, containing the step of administering natural killer cells with the improved tumor cell killing activity to tumor cells.

The killing activity of NK cells is increased in vitro.

The cancer herein is preferably selected from the group consisting of breast cancer, melanoma, stomach cancer, liver cancer, blood cancer, colon cancer, and lung cancer, but not always limited thereto.

To increase the killing activity of NK cells, YC-1 or IL-21 can be treated but co-administration of YC-1 and IL-21 is more preferred.

In addition, the present invention provides a use of YC-1 or IL-21 for the preparation of an agent for differentiating hematopoietic stem cells into natural killer cells or an anti-cancer agent.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Separation of Hematopoietic Stem Cells from Cord Blood

Cord blood provided from Department of Obstetric & Gynecology, Konyang University Hospital, Taejon, Korea, for the purpose of study only was diluted in RPMI 1640 (GIBCO-BRL, USA) at the ratio of 2:1. The prepared cord blood was loaded on the upper part of Ficoll-Paque (Sigma, USA), followed by centrifugation (20,000 rpm, 30 minutes) to separate mononuclear cells (MNC). Erythrocytes were eliminated from the obtained cells and the obtained mononuclear cells were marked with the hematopoietic stem cell marker 'CD34 microbeads'. Then, CD34+ cells were separated by MS/RS column and MACS (Magnetic Activated Cell Sorter). The purity of the obtained CD34+ hematopoietic stem cells (referred as "HSC cells" hereinafter) was measured by FACS (BD Bioscience, Mountainview, Calif.), which was 92% (FIG. 1).

EXAMPLE 2

Differentiation from Hematopoietic Stem Cells of Cord Blood into NK Cells

Figure 2:
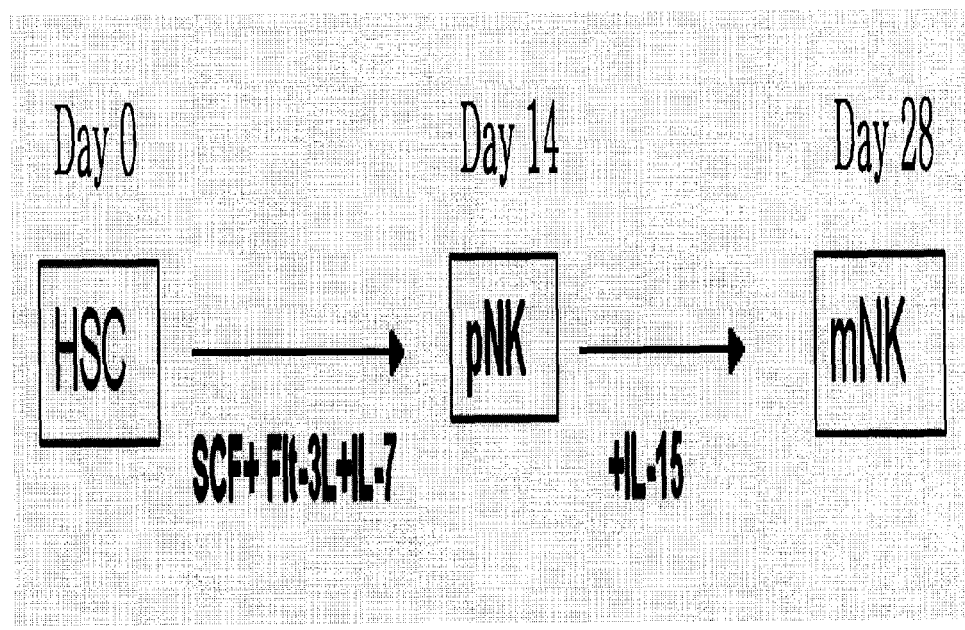
FIG. 2 is a schematic diagram illustrating the process of the differentiation of hematopoietic stem cells separated from human cord blood into mature NK (mNK) cells through NK precursors (pNK):
HSC: hematopoietic stem cells;
SCF: stem cell factor; and
Flt3L: FMS-like tyrosine kinase 3 ligand.
Figure 3:
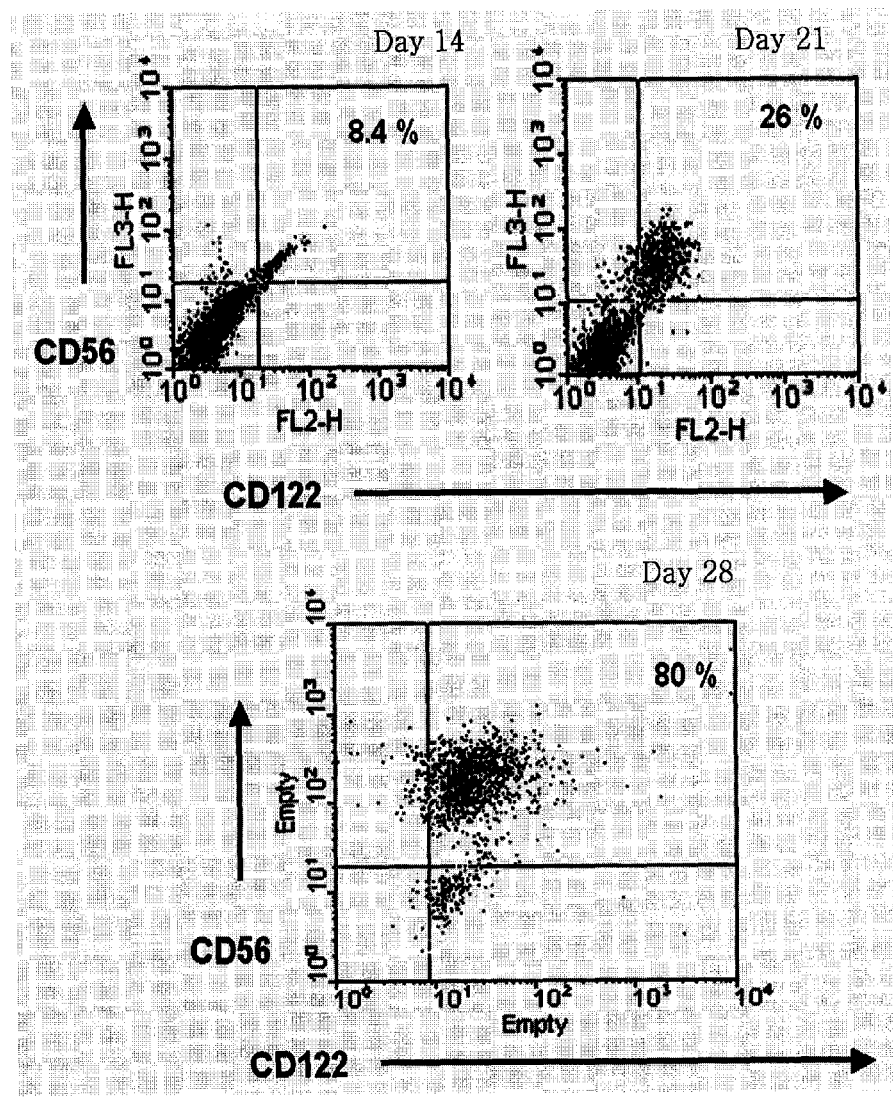
FIG. 3 is a graph illustrating the expression of the surface molecule of each NK cell differentiation stage (the number written in quadrant indicates the purity).

The HSC cells separated from cord blood in Example 1 were inoculated in a 12-well plate (Falcon, USA) containing the Myelocult complete medium (Stem cell Technology, CA) supplemented with 30 ng/ml of human Factor (PeproTech, USA), 50 ng/ml of human Flt3L (FMS-like tyrosine kinase 3 ligand, PeproTech, USA), 5 ng/ml of human IL-7 (PeproTech, USA), and $10^{-6}$ M of hydro SCF (Stem Cell hydrocortisone, Stem cell Technology, CA) at the concentration of $1\times10^6$ cells/well, followed by culture for 14 days in a 37° C., 5% $CO_2$ incubator. Three days later, half of the supernatant was replaced with a fresh medium containing cytokines having the same composition as the above. For the differentiation into mature NK cells (referred as "NK cells" hereinafter), HSC cells were recovered 14 days later and cultured again for 14 days in the presence of human IL-15 (30 ng/ml, PeproTech, USA). Three days later, half of the medium was replaced with a fresh medium containing cytokines having the same composition as the above. (FIG. 2). On the 28th day of culture, the purity of NK cells was measured by using anti-CD56 antibody and the expression of NK cell receptor was measured by flow cytometry (FACS) (FIG. 3).

EXAMPLE 3

Effect on NK Cell Differentiation of IL-21

To investigate the effect on NK cell differentiation of IL-21 known to promote differentiation and increase activity, IL-21 (20 ng/ml, PeproTech, USA) was treated during the process of differentiation from hematopoietic stem cells of cord blood into mature NK cells (mNK) through NK precursor cells (pNK). The cells were cultured in the presence of IL-15, followed by FACS analysis and $^{51}$Cr release assay.

IL-21 has the amino acid sequence represented by SEQ. ID. NO: 1 and the nucleotide sequence represented by SEQ. ID. NO: 2.

Figure 4:
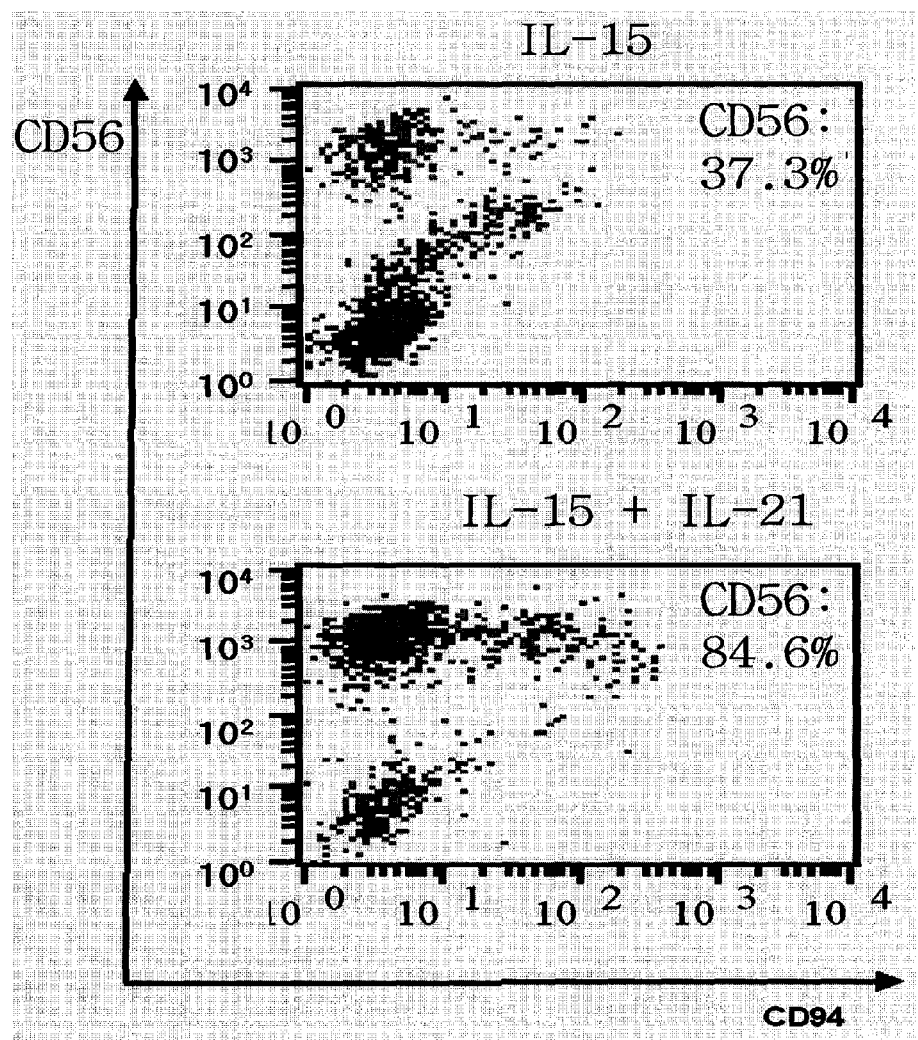
FIG. 4 is a graph illustrating the result of FACS. In differentiation of NK cells, IL-21 was treated to pNKs (NK precursor cells), which were cultured in the presence of IL-15 until they became differentiated into mature NK cells, followed by examination by FACS.
Figure 5:
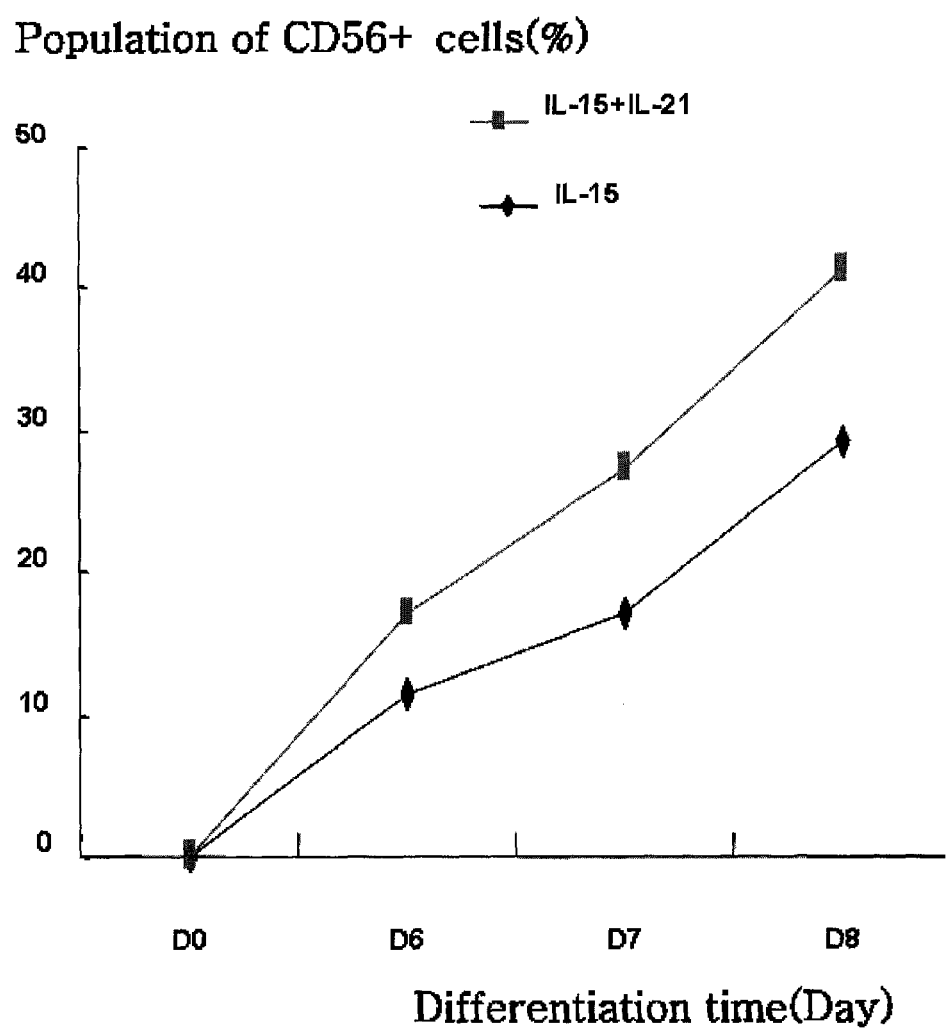
FIG. 5 is a graph illustrating the population of CD56+ NK cells over differentiation time, which is represented by %.

From the result of FACS analysis, it was confirmed that CD56+ NK cell population was increased in IL-21 treated group (FIGS. 4 and 5).

From the result of $^{51}$Cr release assay, it was confirmed that the killing activity of NK cells was increased by IL-21 (FIG. 6). E:T (effector cell:target cell) was 2.5:1.

The above results indicate that IL-21 is involved in NK cell differentiation and directly affects the killing activity of NK cells.

EXAMPLE 4

Effect on NK Cell Differentiation of YC-1

To investigate the effect on NK cell differentiation of YC-1 [3-(5'-hydroxymethyl-2'-furyl)-1-benzylindazole, formula 1] known as an anticancer agent functioning in suppressing HIF-1α activity to inhibit tumor cell growth, YC-1 (1 uM, Sigma) was treated during the process of differentiation from hematopoietic stem cells of cord blood into mature NK cells (mNK) through NK precursor cells (pNK). The cells were cultured in the presence of IL-15, followed by FACS analysis and $^{51}$Cr release assay.

From the result of FACS analysis, it was confirmed that CD56+ NK cell population was increased in YC-1 treated group (FIGS. 7 and 8).

From the result of $^{51}$Cr release assay, it was confirmed that the killing activity of NK cells was increased by YC-1 (FIG. 9). E:T (effector cell:target cell) was 5:1.

The above results indicate that YC-1 is involved in NK cell differentiation and directly affects the killing activity of NK cells.

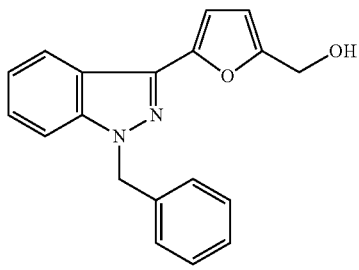

<Formula 1>

EXAMPLE 5

Synergy Effect of IL-21 and YC-1 on NK Cell Differentiation

To investigate synergy effect of IL-21 and YC-1 on NK cell differentiation, IL-21 (10 ng/ml) and YC-1 (0.5 uM) were co-treated during the process of differentiation from hematopoietic stem cells of cord blood into mature NK cells (mNK) through NK precursor cells (pNK). The cells were cultured in the presence of IL-15, followed by FACS analysis. At that time, the concentrations of IL-21 and YC-1 were regulated low in order not to affect NK cell differentiation (10 ng/ml of IL-21 and 0.5 uM of YC-1).

From the result of FACS analysis, NK cells were slightly increased when each of the two was separately treated but NK cells were significantly increased when both of them were treated together (FIGS. 10 and 11), indicating that the co-treatment of IL-21 and YC-1 brings synergy effect.

INDUSTRIAL APPLICABILITY

As explained hereinbefore, YC-1 and IL-21 regulate differentiation of hematopoietic stem cells into natural killer cells and increase the killing activity of NK cells. Therefore, an agent for differentiating hematopoietic stem cells into natural killer cells comprising YC-1 [3-(5'-hydroxymethyl-2'-furyl)-1-benzylindazole] or IL-21 (Interleukin-21) as an active ingredient and a method for differentiating hematopoietic stem cells into natural killer cells using the same can be effectively used for cell therapy for the treatment of cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for differentiating hematopoietic stem cells into natural killer (NK) cells comprising the following steps:
   (i) inducing proliferation of NK precursor cells by adding a NK precursor inducer to hematopoietic stem cells in vitro; and
   (ii) differentiating the NK precursor cells into mature NK cells by adding:
      [3-(5'-hydroxymethyl-2'-furyl)-1-benzylindazole] (YC-1) and interleukin-15 (IL-15); or
      YC-1, interleukin-21 (IL-21), and IL-15 to the NK precursor cells.

2. The method according to claim 1, wherein the NK precursor inducer of step (i) is stem cell factor (SCF) and FMS-like tyrosine kinase 3 ligand (Flt3L).

3. The method according to claim 1, wherein the IL-21 of step (ii) is a protein selected from the group consisting of:
   (a) the protein comprising the amino acid sequence represented by SEQ ID NO: 1; and
   (b) the protein encoded by the DNA containing the coding region of the nucleotide sequence represented by SEQ ID NO: 2.

4. The method according to claim 1, wherein the dosage of the IL-21 of step (ii) is 10 ng/ml-50 ng/ml.

5. The method according to claim 1, wherein the dosage of the YC-1 of step (ii) is 0.5 μM-5 μM.

* * * * *

SEQUENCE LISTING

```
<160> NUMBER OF SEQ ID NOS: 2

<210> SEQ ID NO 1
<211> LENGTH: 162
<212> TYPE: PRT
<213> ORGANISM: Homo sapiens

<400> SEQUENCE: 1

Met Arg Ser Ser Pro Gly Asn Met Glu Arg Ile Val Ile Cys Leu Met
1               5                   10                  15
```

```
Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
                100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
        130                 135                 140

Gln Lys Met Ile His Gln His Leu Ser Ser Arg Thr His Gly Ser Glu
145                 150                 155                 160

Asp Ser

<210> SEQ ID NO 2
<211> LENGTH: 642
<212> TYPE: DNA
<213> ORGANISM: Homo sapiens

<400> SEQUENCE: 2
gctgaagtga aaacgagacc aaggtctagc tctactgttg gtacttatga gatccagtcc      60
tggcaacatg gagaggattg tcatctgtct gatggtcatc ttcttgggga cactggtcca    120
caaatcaagc tcccaaggtc aagatcgcca catgattaga atgcgtcaac ttatagatat    180
tgttgatcag ctgaaaaatt atgtgaatga cttggtccct gaatttctgc cagctccaga    240
agatgtagag acaaactgtg agtggtcagc ttttcctgt tttcagaagg cccaactaaa    300
gtcagcaaat acaggaaaca atgaaaggat aatcaatgta tcaattaaaa agctgaagag    360
gaaaccacct tccacaaatg cagggagaag acagaaacac agactaacat gcccttcatg    420
tgattcttat gagaaaaaac cacccaaaga attcctagaa agattcaaat cacttctcca    480
aaagatgatt catcagcatc tgtcctctag aacacacgga agtgaagatt cctgaggatc    540
taacttgcag ttggacacta tgttacatac tctaatatag tagtgaaagt catttctttg    600
tattccaagt ggaggagccc tattaaatta tataaagaaa ta                        642
```